(12) United States Patent
Mansouri et al.

(10) Patent No.: US 9,956,319 B2
(45) Date of Patent: May 1, 2018

(54) COMPOSITIONS USEFUL AS ANTIBIOFILM OR ANTIMICROBIAL AGENTS AND METHODS USING SAME

(71) Applicant: BAYLOR COLLEGE OF MEDICINE, Houston, TX (US)

(72) Inventors: Mohammad David Mansouri, Houston, TX (US); Rabih O. Darouiche, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 201 days.

(21) Appl. No.: 14/403,671

(22) PCT Filed: May 31, 2013

(86) PCT No.: PCT/US2013/043607
§ 371 (c)(1),
(2) Date: Nov. 25, 2014

(87) PCT Pub. No.: WO2013/181529
PCT Pub. Date: Dec. 5, 2013

(65) Prior Publication Data
US 2015/0165095 A1    Jun. 18, 2015

Related U.S. Application Data

(60) Provisional application No. 61/653,810, filed on May 31, 2012.

(51) Int. Cl.
| | | |
|---|---|---|
| *A61K 31/381* | (2006.01) | |
| *A61K 31/19* | (2006.01) | |
| *A61K 31/65* | (2006.01) | |
| *A61K 31/7036* | (2006.01) | |
| *A61K 31/535* | (2006.01) | |
| *A61L 29/16* | (2006.01) | |
| *A61L 27/54* | (2006.01) | |
| *A61L 31/16* | (2006.01) | |
| *A61L 27/28* | (2006.01) | |
| *A61L 29/08* | (2006.01) | |
| *A61L 31/08* | (2006.01) | |

(52) U.S. Cl.
CPC .............. *A61L 29/16* (2013.01); *A61L 27/28* (2013.01); *A61L 27/54* (2013.01); *A61L 29/08* (2013.01); *A61L 31/08* (2013.01); *A61L 31/16* (2013.01); *A61L 2300/22* (2013.01); *A61L 2300/404* (2013.01)

(58) Field of Classification Search
CPC ...... A61K 31/381; A61K 31/19; A61K 31/65; A61K 31/7036; A61K 31/535; A61L 29/16; A61L 27/54; A61L 31/16
See application file for complete search history.

(56) References Cited

U.S. PATENT DOCUMENTS

| | | | |
|---|---|---|---|
| 6,365,623 | B1 | 4/2002 | Perricone |
| 6,589,591 | B1 | 7/2003 | Mansouri et al. |
| 7,238,363 | B2 | 7/2007 | Mansouri et al. |
| 2005/0271694 | A1 | 12/2005 | Mansouri et al. |
| 2006/0246208 | A1 | 11/2006 | Mansouri et al. |
| 2007/0212381 | A1 | 9/2007 | DiFiore et al. |
| 2008/0063693 | A1 | 3/2008 | Cook et al. |

FOREIGN PATENT DOCUMENTS

| | | | |
|---|---|---|---|
| JP | 2010270014 A | * | 12/2010 |
| KR | 20070108973 A | * | 11/2007 |
| WO | 2007105854 A1 | | 9/2007 |
| WO | 2009137074 A1 | | 11/2009 |

OTHER PUBLICATIONS

STN Accession No. 2010:1500148 CAPLUS (Dec. 3, 2010).*
CAS Registry No. 1077-28-7 (Nov. 16, 1984).*
STN Accession No. 2008:30311 CAPLUS (Jan. 9, 2008).*
An et al., The promise and peril of transcriptional profiling in biofilm communities, Current Opinion in Microbiology 2007, 10:292-296.
Auler et al., Biofilm formation on intrauterine devices in patients with recurrent vulvovaginal candidiasis, Medical Mycology Feb. 2010, 48, 211-216.
Davis et al., Microscopic and physiologic evidence for biofilm-associated wound colonization in vivo, Wound Rep Reg (2008) 16 23-29.
Parsek et al., Bacterial Biofilms: An Emerging Link to Disease Pathogenesis, Annu. Rev. Microbiol. 2003. 57:677-701.

* cited by examiner

*Primary Examiner* — Bethany P Barham
*Assistant Examiner* — Peter Anthopolos
(74) *Attorney, Agent, or Firm* — Riverside Law LLP

(57) ABSTRACT

The present invention includes compositions and methods useful for removing microorganisms and/or biofilm-embedded microorganisms from the surface of a medical device or subject's body. The present invention further includes compositions and methods useful for coating medical devices. The present invention further includes compositions and methods useful for preventing or reducing the growth or proliferation of microorganisms and/or biofilm-embedded microorganisms on the surface of a medical device or subject's body.

48 Claims, 1 Drawing Sheet

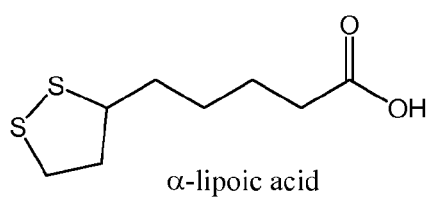
α-lipoic acid
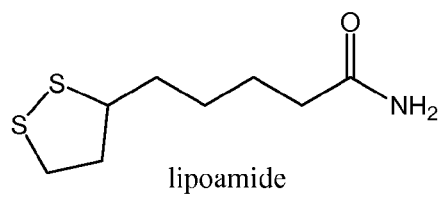
lipoamide
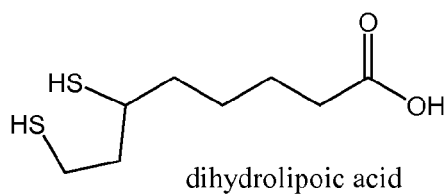
dihydrolipoic acid
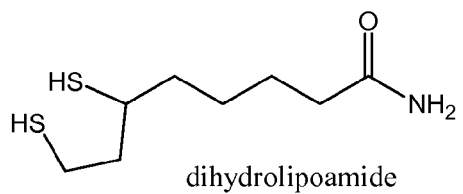
dihydrolipoamide
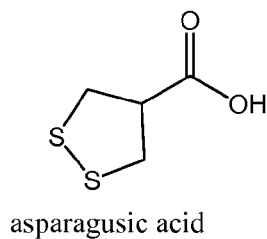
asparagusic acid
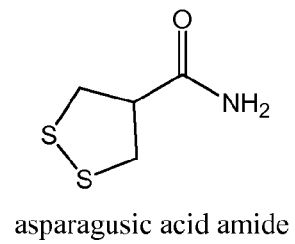
asparagusic acid amide
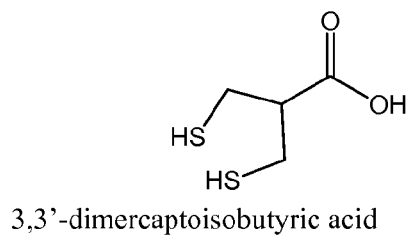
3,3'-dimercaptoisobutyric acid
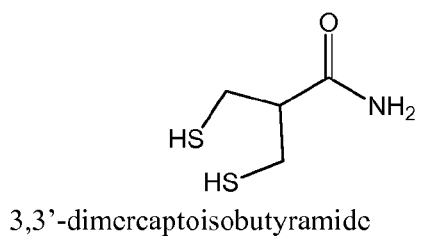
3,3'-dimercaptoisobutyramide

COMPOSITIONS USEFUL AS ANTIBIOFILM OR ANTIMICROBIAL AGENTS AND METHODS USING SAME

CROSS-REFERENCE TO RELATED APPLICATIONS

The present application is the U.S. national phase application filed under 35 U.S.C. § 371 claiming benefit to International Patent Application No. PCT/US13/43607, filed May 31, 2013, which claims priority under 35 U.S.C. § 119(e) to U.S. Provisional Application No. 61/653,810, filed May 31, 2012, which is hereby incorporated by reference in its entirety herein.

BACKGROUND OF THE INVENTION

Microorganisms, such as bacteria, mycobacteria or fungi, may colonize surfaces, forming a structure called "biofilm" as a defense against antimicrobial agents and other environmental hazards. A biofilm is a layer comprising an aggregate of microorganisms, wherein each cell adheres to each other. These adherent cells are frequently embedded within a self-produced matrix of extracellular polymeric substance (EPS)—a polymeric conglomeration generally composed of extracellular DNA, proteins, and polysaccharides. Biofilms may form on living or non-living surfaces and can be prevalent in natural, industrial and hospital settings (Hall-Stoodley et al., 2004, Nature Rev. Microbiol. 2(2):95-108; Lear & Lewis, eds., 2012, "Microbial Biofilms: Current Research and Applications", Caister Academic Press, 2012). The microbial cells growing in a biofilm are physiologically distinct from single planktonic cells of the same organism, which float or swim in a liquid medium.

Microbes form a biofilm in response to factors such as cellular recognition of specific or non-specific attachment sites on a surface; nutritional cues; or exposure to sub-inhibitory concentrations of antibiotics (Karatan & Watnick, 2009, Microbiol. Mol. Biol. Rev. 73(2):31047; Hoffman et al., 2005, Nature 436(7054):1171-5). When a cell switches to the biofilm mode of growth, it undergoes a phenotypic shift in behavior in which large suites of genes are differentially regulated (An & Parsek, 2007, Curr. Op. Microbiol. 10(3):292-6).

Biofilms are involved in as much as 80% of all microbial infections ("Research on microbial biofilms (PA-03-047)," NIH, National Heart, Lung, and Blood Institute, December 2012). Infectious processes in which biofilms have been implicated include common problems (such as urinary tract infections, catheter infections, middle-ear infections, formation of dental plaque, gingivitis, and coating of contact lenses), and less common but more lethal processes (such as endocarditis, infections in cystic fibrosis, and infections of permanent indwelling devices such as joint prostheses and heart valves) (Rogers, 2008, "Molecular Oral Microbiology," Caister Academic Press, pp. 65-108; Imamura et al., 2008, Antimicrob. Agents Chemother. 52(1):171-82; Lewis, 2001, Antimicrob. Agents Chemother. 45(4):999-100; Parsek & Singh, 2003, Ann. Rev. Microbiol. 57:677-701). In fact, bacterial biofilms may impair cutaneous wound healing and reduce topical antibacterial efficiency in healing or treating infected skin wounds (Davis et al., 2008, Wound Rep. Regen. 16(1):23-9).

Biofilms can also be formed on the inert surfaces of implanted devices such as catheters, prosthetic cardiac valves and intrauterine devices (Auler et al., 2009, Med. Mycol. 1-6). Antimicrobial agents (such as antibiotics or antiseptics) are generally not much active in killing or inhibiting the microorganisms that are deeply embedded within the biofilm, in part due to the shielding effect of the biofilm.

There is a need in the art for novel antimicrobial or biofilm-penetrating compositions. These compositions may be used to remove at least a portion of or reduce the number of the microorganisms or biofilm-embedded microorganisms attached to the surface of a medical device or the surface of a subject's body. These compositions may also be used to coat medical devices, thus inhibiting microbial growth or disrupting the biofilm and allowing antimicrobial agents and/or antifungal agents to penetrate the biofilm and kill the microorganisms located therein. These compositions may also be used to prevent or reduce the growth or proliferation of microorganisms or biofilm-embedded microorganisms on the surface of a medical device or on the surface of a subject's body. The present invention fulfills these needs.

BRIEF SUMMARY OF THE INVENTION

The invention includes a method of preventing or reducing the growth or proliferation of microorganisms or biofilm-embedded microorganisms on at least one surface of a medical device or subject's body. The method comprises providing at least one surface of (i) a medical device, or (ii) a subject's body. The method further comprises providing a composition comprising α-lipoic acid or an analog thereof. The method further comprises contacting the at least one surface with the composition in an amount sufficient to prevent or reduce the growth or proliferation of microorganisms or biofilm-embedded microorganisms on the at least one surface.

In one embodiment, in (ii) the subject is a mammal. In another embodiment, the mammal is human. In yet another embodiment, the composition further comprises a base material. In yet another embodiment, the composition further comprises at least one additional antimicrobial agent. In yet another embodiment, α-lipoic acid or an analog thereof and the at least one additional antimicrobial agent act synergistically to prevent or reduce the growth or proliferation of microorganisms or biofilm-embedded microorganisms on the at least one surface.

In one embodiment, the composition is contacted with the at least one surface for a period of time sufficient to form a coating of the composition on the at least one surface. In another embodiment, the contacting of the at least one surface of the medical device in (i) with the composition comprises incorporating the composition into the material used to prepare the medical device. In yet another embodiment, the composition is contacted with the medical device in (i) by flushing the medical device with the composition for a period of time sufficient to prevent or reduce the growth or proliferation of microorganisms or biofilm-embedded microorganisms on the at least one surface of the medical device.

In one embodiment, the medical device in (i) is non-metallic and the composition further comprises an acidic solution and glycerol. In another embodiment, the acidic solution comprises a short chain monocarboxylic acid and ortho-phosphoric acid. In yet another embodiment, the acidic solution comprises monocarboxylic acid, ortho-phosphoric acid and glycerol in a ratio of about 79:8:13 (v/v/v).

In one embodiment, the device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof.

In one embodiment, the composition is applied to at least one surface to form a first layer, and optionally the first layer is allowed to dry. In another embodiment, a second composition comprising a cyanoacrylate is applied on the first layer to form a second layer, and optionally the second layer is allowed to dry. In yet another embodiment, the matrix component comprises hide powder and collagen, wherein the hide powder is at an about 5% to about 50% (w/v) concentration and the collagen is at an about 0.1% to about 20% (w/v) concentration. In yet another embodiment, the acidic component is an acid solvent or acidic solution. In yet another embodiment, the glycerol is present in the matrix component at a concentration between about 0.5% and about 10%. In yet another embodiment, a cyanoacrylate coat is applied to the at least one surface as a primer before applying the composition.

The invention further includes a coated medical device having at least one surface, wherein the at least one surface is coated with a composition. In one embodiment, the coating of the at least one surface prevents or reduces the growth or proliferation of microorganisms or biofilm-embedded microorganisms on the at least one surface, wherein the composition comprises α-lipoic acid or an analog thereof.

In one embodiment, the composition further includes a base material. In another embodiment, the composition further comprises at least one additional antimicrobial agent. In yet another embodiment, the coating of the at least one surface is achieved by incorporating the composition in the material used to prepare the medical device.

In one embodiment, the device is non-metallic and the composition further comprises an acidic solution and glycerol. In another embodiment, the acidic solution comprises a short chain monocarboxylic acid and ortho-phosphoric acid. In yet another embodiment, the acidic solution comprises monocarboxylic acid, ortho-phosphoric acid and glycerol in a ratio of about 79:8:13 (v/v/v).

In one embodiment, the method of coating the at least one surface comprises the steps of contacting the at least one surface with the composition; removing excess of the composition from the at least one surface; and drying the at least one surface.

In one embodiment, the device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof. In another embodiment, the at least one surface is coated with a second composition comprising a cyanoacrylate. In yet another embodiment, the matrix component comprises hide powder and collagen, wherein the hide powder is at an about 5% to about 50% (w/v) concentration and the collagen is at an about 0.1% to about 20% (w/v) concentration. In yet another embodiment, the acidic component is an acid solvent or acidic solution. In yet another embodiment, the glycerol is present in the matrix component at a concentration between about 0.5% and about 10%.

The invention further comprises a method for removing at least a portion of or reducing the number of microorganisms or biofilm-embedded microorganisms attached to at least one surface of a medical device or subject's body. The method comprises providing at least one surface of (i) a medical device or (ii) a subject's body, wherein the microorganisms or biofilm-embedded microorganisms are attached to the at least one surface. The method further comprises providing a composition comprising α-lipoic acid or an analog thereof. The method further comprises contacting the composition with the at least one surface in an amount sufficient to remove at least a portion of or reduce the number of microorganisms or biofilm-embedded microorganisms attached to the at least one surface.

In one embodiment, in (ii) the subject is a mammal. In another embodiment, the mammal is human. In yet another embodiment, the composition further comprises a base material. In yet another embodiment, the composition further comprises at least one additional antimicrobial agent. In yet another embodiment, α-lipoic acid or an analog thereof and the at least one additional antimicrobial agent act synergistically to prevent or reduce the growth or proliferation of microorganisms or biofilm-embedded microorganisms on the at least one surface.

In one embodiment, the composition is contacted with the at least one surface for a period of time sufficient to form a coating of the composition on the at least one surface. In another embodiment, the contacting of the at least one surface of the medical device in (i) with the composition comprises incorporating the composition into the material used to prepare the medical device. In yet another embodiment, the composition is contacted with the medical device by flushing the medical device with the composition for a period of time sufficient to remove at least a portion of or reduce the number of microorganisms or biofilm-embedded microorganisms attached to at least one surface of the medical device.

In one embodiment, the medical device in (i) is non-metallic and the composition further comprises an acidic solution and glycerol. In another embodiment, the acidic solution comprises a short chain monocarboxylic acid and ortho-phosphoric acid. In yet another embodiment, the acidic solution comprises monocarboxylic acid, ortho-phosphoric acid and glycerol in a ratio of about 79:8:13 (v/v/v).

In one embodiment, the metallic device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof.

In one embodiment, the composition is applied to at least one surface to form a first layer, and optionally the first layer is allowed to dry. In another embodiment, a second composition comprising a cyanoacrylate is applied on the first layer to form a second layer, and optionally the second layer is allowed to dry. In yet another embodiment, the matrix component comprises hide powder and collagen, wherein the hide powder is at an about 5% to about 50% (w/v) concentration and the collagen is at an about 0.1% to about 20% (w/v) concentration. In yet another embodiment, the acidic component is an acid solvent or acidic solution. In yet another embodiment, the glycerol is present in the matrix component at a concentration between about 0.5% and about 10%. In yet another embodiment, a cyanoacrylate coat is applied to the at least one surface as a primer before applying the composition.

The invention further includes a composition comprising α-lipoic acid or an analog thereof and at least one additional antimicrobial agent, wherein the α-lipoic acid or analog thereof and the at least one additional antimicrobial agent have synergistic antimicrobial activity.

In one embodiment, the antimicrobial activity is selected from the group consisting of antibacterial, antimycobacterial, antifungal, antiviral and any combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a non-limiting illustration of compounds useful within the compositions and methods of the invention.

DETAILED DESCRIPTION OF THE INVENTION

The present invention relates to the unexpected discovery that α-lipoic acid or an analog thereof (FIG. 1) acts as an antimicrobial or antibiofilm agent. In one embodiment, α-lipoic acid or the analog thereof has an antimicrobial activity selected from the group consisting of antibacterial, antimycobacterial, antifungal, antiviral and any combinations thereof. α-Lipoic acid or an analog thereof may be used, alone or in combination with at least one additional antimicrobial agent, to prepare antimicrobial and/or biofilm-penetrating compositions. In one embodiment, α-lipoic acid or an analog thereof and the at least one additional antimicrobial agent act synergistically in preventing, reducing or disrupting microbial growth, and/or preventing, reducing or disrupting formation of a biofilm on a surface.

The compositions of the invention find use in removing at least a portion of or reducing the number of microorganisms and/or biofilm-embedded microorganisms attached to the surface of a medical device or the surface of a subject's body (such as the skin of the subject, or a mucous membrane of the subject, such as the vagina, anus, throat, eyes or ears). The compositions of the invention find further use in coating the surface of a medical device, thus inhibiting or disrupting microbial growth and/or inhibiting or disrupting the formation of biofilm on the surface of the medical device. The compositions of the invention find further use in preventing or reducing the growth or proliferation of microorganisms and/or biofilm-embedded microorganisms on the surface of a medical device or on the surface of a subject's body. However, the invention is not limited to applications in the medical field. Rather, the invention includes using α-lipoic acid or an analog thereof as an antimicrobial and/or anti-biofilm agent in any setting.

In one embodiment, α-lipoic acid or an analog thereof disrupts the biofilm of microorganisms and attacks the microorganism. In another embodiment, α-lipoic acid or an analog thereof allows at least one additional antimicrobial agent (e.g., an antiseptic, antibiotic, antifungal or antiviral agent) present in the composition to eliminate the microorganisms and/or biofilm-embedded microorganisms from at least one surface of the medical device or at least one surface of the subject's body, or inhibit or disrupt the proliferation of microorganisms and/or biofilm-embedded microorganisms on at least one surface of the medical device or at least one surface of the subject's body. Specifically, the compositions of the invention may prevent or reduce the proliferation of microorganisms and/or biofilm-embedded microorganisms, or remove at least a portion of such microorganisms, on at least one surface of the medical device or at least one surface of the subject's body.

In one aspect, the compositions of the invention may be in the form of a coating that is applied to the surface of a medical device or the surface of a subject's body. In one embodiment, the coating prevents or hinders microorganisms and/or biofilm-embedded microorganisms from growing and proliferating on at least one surface of the medical device or at least one surface of the subject's body. In another embodiment, the coating facilitates access of antimicrobial agents to the microorganisms and/or biofilm-embedded microorganisms, thus helping prevent or hinder the microorganisms and/or biofilm-embedded microorganisms from growing or proliferating on at least one surface of the medical device or at least one surface of the subject's body. The compositions of the invention may also be in the form of a liquid or solution, used to clean the surface of medical device or the surface of a subject's body, on which microorganisms and/or biofilm-embedded microorganisms live and proliferate. Such cleaning of the medical device or body surface may occur by flushing, rinsing, soaking, or any additional cleaning method known to those skilled in the art, thus removing at least a portion of or reducing the number of microorganisms and/or biofilm-embedded microorganisms attached to at least one surface of the medical device or at least one surface of the subject's body.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the terms "or" and "and/or" are used interchangeably.

As used herein, the term "about" is understood by persons of ordinary skill in the art and varies to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, "α-lipoic acid" refers any compound selected from the group consisting of the (R)-enantiomer of α-lipoic acid, the (S)-enantiomer of α-lipoic acid, any salt or hydrate thereof, and any combinations thereof "α-Lipoic acid" may also refer to a composition comprising about equimolar amounts of the (R)- and (S)-enantiomers of α-lipoic acid (such mixture is commonly referred to as racemic α-lipoic acid).

As used herein, a "microorganism" refers to any microorganism that may colonize or proliferate on the surface of a medical device (or in proximity of a medical device within the body) or on a body surface, including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, a "biofilm-embedded microorganism" refers to any microorganism that forms or nests within a biofilm during colonization and proliferation on the surface of a medical device or on a body surface, including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, the term "biocompatible" as applied to a medical device refers to a medical device that is compatible with living tissues, such that the medical device is not rejected or does not cause harm to the living tissue.

As used herein, the term "biocompatible polymer" refers to a polymeric material that does not cause inflammatory or immune response in the body. As used herein, the term "biodegradable polymer" refers to a polymeric material that undergoes degradation when placed inside the body and generates non-toxic degradation products, which may be eliminated by the body as such or metabolized into one or more non-toxic molecules. Non-limiting examples of biodegradable biocompatible polymers are: polyglycolide or polyglycolic acid (PGA); polylactide or polylactic acid (PLA); poly-L-lactic acid (PLLA); poly-D/L-lactic acid with polyglycolic acid (PDLLA-co-PGA); poly-L-lactic acid-co-glycolic acid (PLGA); PDLLA with bioactive glass; PLGA with bioactive glass; poly-L-lactic acid with β-tricalcium phosphate (PLLA-TCP); poly-L-lactic acid with hydroxyapatite (PLLAHA); polydioxanone (PDS); polyethylene glycol (PEG); poly(ε-caprolactone) (PCL); polycaprolactone (PCL) with alginate; polyhydroxybutyrate (PHB); polycarbonate (PC); N-vinyl pyrrolidone copolymers; polyorthoester; chitosan; poly(2-hydroxyethyl-methacrylate) (PHEMA); hyaluronic acid and hydrogels.

As used herein, "cyanoacrylate" refers to cyanoacrylate compounds as they are commonly known in the art. These include, but are not limited to, methyl cyanoacrylate, ethyl cyanoacrylate, butyl cyanoacrylate, octyl cyanoacrylate (including anyone or more of N-octyl-cyanoacrylate, 2-octyl cyanoacrylate, iso-octyl cyanoacrylate), hexyl cyanoacrylate, decyl cyanoacrylate, methoxy ethyl cyanoacrylate, isoamyl cyanoacrylate, and isopropyl cyanoacrylate. The term "cyanoacrylate" encompasses a pure cyanocraylate, a mixture of pure cyanoacrylates, or a solution of one or more cyanoacrylates. One of ordinary skill in the art will recognize other possible candidates.

As used herein, the term "organic solvent" refers to solvents including, but not limited to, alcohols (e.g., methanol and ethanol), ketones (e.g., acetone and methylethylketone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the term "alkalinizing agent" refers to an organic and inorganic base, including sodium hydroxide, potassium hydroxide, alkyl hydroxides, ammonia in water (27% ammonium hydroxide), diethylamine and triethylamine.

As used herein, the term "high ionic strength salt" refers to a salt exhibiting high ionic strength, such as sodium chloride, potassium chloride, or ammonium acetate. These salts may act both as an alkalinizing agent and as a penetrating agent to enhance the reactivity of the surface of the medical device or subject's body. Therefore, in one specific embodiment, high ionic strength salts may also be used in the step of forming the biofilm-penetrating composition.

As used herein, the term "base material" refers to any material that effectively disperses α-lipoic acid or an analog thereof at an effective concentration to contact the microorganisms and/or penetrate or disrupt the biofilm. The base material thus facilitates access of α-lipoic acid or analog thereof, antimicrobial agent, and/or antifungal agent to the microorganisms on the surface and/or embedded in the biofilm, thus removing at least a portion of or reducing the number of microorganisms attached to at least one surface of the medical device or subject's body. The term "base material" also includes any solution that effectively disperses α-lipoic acid or analog thereof at an effective concentration to form a composition coating for a medical device, which prevents or reduces the growth or proliferation of microorganisms and/or biofilm-embedded microorganisms on at least one surface of the medical device. In the case of the composition coating, the base material may also facilitate the adhesion of the composition to at least one surface of the medical device, thus preventing the composition coating from being easily removed from the surface of the medical device.

As used herein, the medical devices amenable to treatment according to one aspect of the present invention may be "metallic" or "non-metallic". Additionally, the metallic or non-metallic portion, or both, of devices having both metallic and non-metallic portions may be treated. Treatable medical devices may also include devices that are formed from more than one type of non-metallic or metallic material.

"Non-metallic" materials that can be treated by the method of the present invention include, but are not limited to, rubber, plastic, ceramic, nylon, silicone, silicon, germanium, tin, gallium arsenide, polyurethane, polyethylene, polyvinyl chloride, carbon, carbon fibers, carbon polymer, Gortex® (polytetrafluoroethylene tetraphthalate), Dacron® (polyethylene tetraphthalate), Teflon® (polytetrafluoroethylene or PTFE), expanded polytetrafluoroethylene (ePTFE), latex, elastomers, polymers, bioabsorbable polymers (including, but not limited to, polyglycolic acid (PGA), polylactide-co-glycolide, and polylactic acid (PLA) and non-bioabsorbable polymers (e.g., polymethyl methacrylate), gelatin, collagen, globulin, or albumin. Any combination thereof is also possible. One of ordinary skill in the art will recognize other possible candidates.

"Metallic" devices treatable by the method of the present invention include, but are not limited to, all of the conventional metals and metal alloys commonly used in medical implants, including, but not limited to, cobalt-chromium, titanium, stainless steel, tivanium, gold, silver, zirconium, hafnium, and others, including any alloys thereof. In addition, any non-conventional metals or metal alloys are also treatable by the method of the present invention.

As used herein, the term "contacting" includes, but is not limited to, impregnating, compounding, mixing, integrating, coating, rubbing, painting, spraying, immersing, rolling, smearing and dipping.

As used herein, the term "treatment" or "treating," is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of medicine or pharmacology. In one embodiment, the condition is selected from the group consisting of a bacterial infection, fungal infection, mycobacterial infection, viral infection, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal Non-human mammals include, for example, livestock and pets, such as ovine, bovine, porcine, canine, feline and murine mammals. Preferably, the patient, subject or individual is human.

As used herein, the term "composition" or "pharmaceutical composition" refers to a mixture of at least one compound useful within the invention with a pharmaceutically acceptable carrier. The pharmaceutical composition facilitates administration of the compound to a patient or subject, or use of the compound within the methods of the invention. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a non-toxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Effective amount" also refers to a sufficient amount of α-lipoic acid or an analog thereof to prevent or reduce the growth or proliferation of microorganisms and/or biofilm-embedded microorganisms on the at least one medical device surface or body surface, in the case of the composition being a coating. "Effective amount" also refers to a sufficient amount of α-lipoic acid or an analog thereof to penetrate, or break-up, at least a portion of the biofilm on at least one surface of the medical device or subject's body, thereby facilitating access of α-lipoic acid or the analog thereof, antimicrobial agent, and/or antifungal agent to the microorganisms embedded in the biofilm, thus removing at least a portion of or reducing the number of microorganisms attached to at least one surface of the medical device or subject's body. The amount may vary for each compound considered within the compositions of the invention, and upon known factors such as the pharmaceutical characteristics, type of medical device or body surface, degree of biofilm-embedded microorganism contamination, and the use and length of use. It is within the ability of a person of ordinary skill in the art to relatively easily determine an effective concentration for each compound considered within the compositions of the invention.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "container" includes any receptacle for holding the compositions of the invention. For example, in one embodiment, the container is the packaging that contains any of the compositions of the invention. In other embodiments, the container is not the packaging that contains any of the compositions of the invention, i.e., the container is a receptacle, such as a box or vial that contains the packaged or unpackaged composition and the instructions for use of the composition. Moreover, packaging techniques are well known in the art. It should be understood that the instructions for use of the composition may be contained on the packaging containing the composition, and as such the instructions form an increased functional relationship to the packaged product. However, it should be understood that the instructions may contain information pertaining to the compound's ability to perform its intended function within the methods of the invention.

"Instructional material," as that term is used herein, includes a publication, a recording, a diagram, or any other medium of expression that may be used to communicate the usefulness of the compounds and/or methods of the invention. In some instances, the instructional material may be part of a kit useful for treating the surface of a medical device or effecting alleviating or treating the various diseases or disorders recited herein. Optionally, or alternately, the instructional material may describe one or more methods of treating the surface of a medical device or alleviating the diseases or disorders in a cell or a tissue of a mammal. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the composition; or instructions for use of a formulation of the composition.

Compositions

The compositions useful within the invention comprise α-lipoic acid or an analog thereof. As used herein, "α-lipoic acid" refers to any compound selected from the group consisting of the (R)-enantiomer of α-lipoic acid, the (S)-enantiomer of α-lipoic acid, any salt or hydrate thereof, and any combinations thereof, including a composition comprising about equimolar amounts of the (R)- and (S)-enantiomers of α-lipoic acid (such mixture is commonly referred to as racemic α-lipoic acid). α-Lipoic acid has the structure depicted in FIG. 1, and is also commonly known as thioctic acid, 1,2-dithiolane-3-pentanoic acid, 1,2-dithiolane-3-valeric acid or 6,8-dithiooctanoic acid.

Analogs of α-lipoic acid contemplated within the invention include lipoamide (also known as 6,8-thioctic acid amide and α-lipoic amide), dihydrolipoic acid (also known as 6,8-dimercaptooctanoic acid), dihydrolipoamide, ester derivatives of α-lipoic acid, ester derivatives of dihydrolipoic acid, asparagusic acid, ester derivatives of asparagusic acid, 3,3'-dimercapto-isobutyric acid, ester derivatives of 3,3'-dimercapto-isobutyric acid, any salt or solvate thereof, or any combinations thereof. Non-limiting examples of the analogs contemplated within the invention are illustrated in FIG. 1. Ester derivatives of an acid useful within the invention include, but are not limited to, methyl, ethyl, propyl, isopropyl, n-butyl, sec-butyl, isobutyl, tert-butyl, n-pentyl, n-hexyl, benzyl, and stearyl esters.

The compositions useful within the invention may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, α-lipoic acid or an analog thereof and the at least one additional antimicrobial agent act synergistically in preventing, reducing or disrupting microbial growth or formation of a biofilm on a surface. A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv.

Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The compositions useful within the invention may further include a microbial activity indicator, which is capable of indicating the presence of microorganisms on the surface of a medical device.

The composition useful within the invention may further comprise an acidic solution and glycerol. The acidic solution may comprise a short chain monocarboxylic acid (e.g., formic acid, acetic acid or propionic acid). The acidic solution may further comprise ortho-phosphoric acid. In one embodiment, the acidic solution further comprises a salt, such as potassium chloride.

In one preferred embodiment, α-lipoic acid or an analog thereof is present in the composition in an amount sufficient to penetrate or disrupt a biofilm and allow access of the α-lipoic acid or analog thereof, and/or the at one additional antimicrobial agent to the biofilm-embedded microorganism, thereby facilitating the removal of at least a portion of the biofilm-embedded microorganisms from at least one surface of the medical device or subject's body. In another preferred embodiment, α-lipoic acid or an analog thereof is present in the composition in an amount sufficient to inhibit the growth or proliferation of microorganisms on the surface of the medical device or subject's body, thereby facilitating the removal of at least a portion of the biofilm-embedded microorganisms from such surface. The α-lipoic acid or analog thereof may constitute about 0.01% to about 100% (by weight) of the composition, preferably about 0.1% to about 60% (by weight) of the composition, and more preferably about 0.5% to about 30% (by weight) of the composition.

The composition of the invention may further comprise a base material and a biofilm-penetrating agent. Non-limiting examples of suitable base materials include, but are not limited to, buffer solutions, phosphate buffered saline, saline, water, polyvinyl, polyethylene, polyurethane, polypropylene, polysiloxane (e.g., silicone elastomers and silicone adhesives), polycarboxylic acids, (e.g., polyacrylic acid, polymethacrylic acid, polymaleic acid, poly(maleic acid monoester), polyaspartic acid, polyglutamic acid, aginic acid or pectimic acid), polycarboxylic acid anhydrides (e.g., polymaleic anhydride, polymethacrylic anhydride or poly acrylic acid anhydride), polyamines, polyamine ions (e.g., polyethylene imine, polyvinylarnine, polylysine, poly-(dialkylamineoethyl methacrylate), poly(d-ialkylaminomethyl styrene) or poly-(vinylpyridine)), poly ammonium ions (e.g., poly-(2-methacryloxyethyl trialkyl ammonium ion), poly-(vinylbenzyl trialkyl ammonium ions), poly-(N-alkylypyridinium ion) or poly(dialkyloctamethylene ammonium ion) and polysulfonates (e.g. poly-(vinylsulfonate) or poly-(styrene sulfonate)), collodion, nylon, rubber, plastic, polyesters, Gortex® (polytetrafiuoroethylene), Dacron® (polyethylene tetraphthalate), Teflon® polytetrafiuoroethylene), latex and derivatives thereof, elastomers and Dacron® sealed with gelatin, collagen or albumin, cyanoacrylates, methacrylates, papers with porous barrier films, adhesives (e.g., hot melt adhesives, solvent based adhesives, and adhesive hydrogels), fabrics, and crosslinked and non-crosslinked hydrogels, and any other polymeric materials that facilitate dispersion of the biofilm-penetrating agent and adhesion of the biofilm-penetrating coating to at least one surface of the medical device or subject's body. Linear copolymers, cross-linked copolymers, graft polymers, and block polymers, containing monomers as constituents of the above exemplified polymers may also be used.

In the case of internal or external use of the biofilm-penetrating composition on humans or animals, α-lipoic acid or an analog thereof and the base material should be biocompatible with the human beings or animals in which the medical device is inserted or implanted, or on which body surface the composition is applied.

The invention further includes a coated medical device, which includes a composition coating applied to at least one surface of the medical device. The composition may be applied to at least one surface of the medical device in any suitable manner, as described herein or as known to those skilled in the art. In one embodiment, a septum, or adhesive layer, is made of a breathable material that has small enough porosity to allow moisture to pass, but functions as a barrier to microorganisms thereby facilitating a lower incidence of microorganism colonization and resulting contamination or infection. The adhesive layer may also include a layer of gauze to facilitate a lower incidence of microorganism colonization and resulting contamination or infection.

Medical Devices

The invention contemplates applying to or coating medical devices with the compositions useful within the invention. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the invention is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In one specific embodiment, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In one embodiment, the biofilm-penetrating composition is applied to the entire medical device.

Methods

The invention includes a method of preventing or reducing the growth or proliferation of microorganisms and/or biofilm-embedded microorganisms on at least one surface of a medical device or subject's body. The method includes the steps of: providing at least one surface of (i) a medical device or (ii) a subject's body; providing a composition comprising α-lipoic acid or an analog thereof, and applying the composition to at least one surface in an amount sufficient to prevent or reduce the growth or proliferation of microorganisms or biofilm-embedded microorganisms on at least one surface of the medical device or subject's body.

In one embodiment, the composition further comprises a base material. In another embodiment, preparation of the composition comprises contacting the α-lipoic acid or analog thereof and the base material at room temperature and mixing the resulting mixture for a time sufficient to evenly disperse the α-lipoic acid or analog thereof in the composition prior to contacting the medical device or body surface with the composition. The concentration of α-lipoic acid or an analog thereof in the composition may be varied as desired or necessary to decrease the amount of time the composition is in contact with the medical device or body surface. These variations in concentration of α-lipoic acid or an analog thereof are easily determined by persons skilled in the art. In another embodiment, at least one surface of the medical device or subject's body is contacted with the composition under conditions wherein the composition covers at least one surface of the medical device or subject's body.

In one embodiment, the composition further comprises an organic solvent or an alkalinizing agent, either of which enhances the reactivity of the surface of the medical device with the composition. In another embodiment, the organic solvent and/or alkalinizing agent facilitates adhesion of the composition to at least one surface of the medical device or subject's body.

In one embodiment, the method includes preparing the composition at a concentration that is effective within the methods of the invention. The composition useful within the method comprises α-lipoid acid or an analog, one or more organic solvents, and an alkalinizing agent, and may be heated to a temperature ranging from about 5° C. to about 80° C. to enhance the adherence of the composition coating. The composition may be applied to at least one surface of the medical device or subject's body, preferably by contacting the composition to the at least one surface of the medical device or subject's body for a sufficient period of time for the composition coating to adhere to at least one surface of the medical device or subject's body. The medical device may then be removed from the composition and allowed to dry for at least 8 hours, and preferably, overnight in the dark, at room temperature. The medical device may then be rinsed with a liquid, such as water or an aqueous solution, and allowed to dry for at least 2 hours, and preferably 4 hours, before being sterilized. To facilitate drying of the composition onto the surface of the medical device, the medical device may be placed into a heated environment such as an oven. For example, the medical device may be placed into an oven up to 60° C. for fifteen minutes to facilitate drying the composition onto the surface of a medical device. Preferably, multiple layers of the composition coating is applied to the at least one surface of the medical device by repeating the steps described elsewhere herein.

In one embodiment, the medical device is non-metallic and the composition further comprises an acidic solution and glycerol. In another embodiment, the acidic solution may comprise a short chain monocarboxylic acid (e.g., formic acid, acetic acid or propionic acid). In yet another embodiment, the acidic solution may comprise ortho-phosphoric acid. In yet another embodiment, the acidic solution further comprises a salt, such as potassium chloride. In yet another embodiment, the acidic solution comprises monocarboxylic acid, ortho-phosphoric acid and glycerol in a ratio of about 79:8:13 (v/v/v). In another embodiment, the non-metallic medical device is contacted with the composition for about 10 minutes to about 18 hours, preferably about 60 minutes. In yet another embodiment, the method of treating the non-metallic medical device may further comprise removing excess composition from the non-metallic medical device after the application step and then drying the non-metallic medical device. The non-metallic medical device may be dried for about 16 hours. In yet another embodiment, the non-metallic medical device may be flushed with water after the drying step and may then be dried again for about 10 hours to about 24 hours.

In one embodiment, the medical device is metallic. Non-limiting methods for modification of metallic medical prostheses are described in U.S. Pat. No. 7,238,363, incorporated herein in its entirety by reference. In another embodiment, the composition further comprises an acidic component, a matrix component selected from the group consisting of hide powder, collagen, gelatin, cartilage, tendon, ligament, bone, keratin, fibrin, albumin, globulin, hydroxylapatite, and any combination thereof; and glycerol. The composition is then applied to at least a portion of the medical device to form a first layer. A second composition comprising a cyanoacrylate is formed, and then applied on the first layer to form a second layer. In yet another embodiment, the method further comprises drying the first layer. In yet another embodiment, the drying is performed in the dark. In yet another embodiment, the method further comprises drying the second layer. In yet another embodiment, the method further comprises drying the first layer and drying the second layer. In yet another embodiment, the matrix component is a combination of hide powder and collagen, wherein the hide powder is at a 5% to 50% (w/v) concentration and the collagen is at a 0.1% to 20% (w/v) concentration in the first solution. In yet another embodiment, the acidic component is an acid solvent or acidic solution, and the acid solvent or acidic solution is combined with the hide powder or collagen at a temperature range of 25° C. to 90° C. and mixed until a clear homogeneous solution is obtained. In yet another embodiment, the glycerol is added to a final concentration between 0.5% and 10%. In yet another embodiment, the glycerol in the first composition is added after the therapeutic agent, the acidic component, and the matrix component. In yet another embodiment, the step of applying the first composition to at least a portion of the medical device is selected from the group consisting of immersing the medical device in the composition, spraying the first composition onto the medical device, pouring the first composition over the medical device, blotting the first composition on the medical device, smearing the first composition on the medical device, rolling the medical device in the first composition, brushing the first composition on the medical device, and any combination thereof. In yet another embodiment, the method further comprises drying the first layer from about 1 hour to about 24 hours. In yet another embodiment, the first layer is dried for about 16 hours. In yet another embodiment, the method further comprises drying the second layer from about 5 minutes to about 18 hours. In yet another embodiment, the second layer is dried for about 12 hours. In yet another embodiment, the method further comprises applying a cyanoacrylate coat as a primer before applying the first composition. In yet another embodiment, the method further comprises controlling the viscosity of the second composition comprising a cyanoacrylate. In yet another embodiment, the method further comprises controlling the temperature of the second composition comprising a cyanoacrylate. In yet another embodiment, the method further comprises exposing the coating device to moisture after applying the second composition on the first layer. In yet another embodiment, the first composition comprises hide powder at a concentration of about 29% 10 (w/v). In yet another embodiment, the first composition comprises collagen at a concentration of about 0.5% (w/v). In yet another embodiment, the first composition comprises glycerol at a concentration of about 1.25% (w/v).

One skilled in the art will recognize that the coating or impregnating methods useful within the methods of the invention include all appropriate coating or impregnating methods known in the art. In a non-limiting example, the methods of the invention may utilize the coating methods described in U.S. Pat. No. 6,589,591, which is hereby incorporated herein by reference in its entirety. In one embodiment, the medical device is non-metallic and is treated with a solution comprising butyl acetate/methanol (for example, in a ratio of 85:15) or formic acid/potassium chloride/phosphoric acid/glycerin (for example, in a ratio of 30 ml:400 mg:3 mL:5 mL). In another embodiment, the medical device is immersed in the treatment solution for 60 minutes in the dark.

In one embodiment, the method for coating the medical device with a composition includes incorporating the composition into the material forming the medical device during preparation of the medical device. For example, the composition may be combined with the material forming the medical device, e.g., silicone, polyurethane, polyethylene, Gortex (polytetrafluoroethylene), Dacron® (polyethylene tetraphthalate), Teflon® (polytetrafluoroethylene), and/or polypropylene, and extruded with the material forming the medical device, thereby incorporating the composition into material forming the medical device. In this embodiment, the composition may be incorporated in a septum or adhesive placed at the medical device insertion or implantation site.

In one embodiment, the invention contemplates a single layer or coating of the composition is provided. In another embodiment, the invention contemplates two or more layers or coatings of composition. The multiple layers of the composition are preferably applied to at least one surface of the medical device or subject's body by repeating the coating steps discussed elsewhere herein. In one embodiment, the medical device or subject's body is contacted with the composition three times, allowing the composition to dry on at least one surface of the medical device or subject's body prior to contacting the medical device or subject's body with the composition for each subsequent layer. The medical device thus includes three coats or layers of the composition on at least one surface of the medical device.

The invention also includes a method of removing at least a portion of or reducing the number of microorganisms and/or biofilm embedded microorganisms attached to at least one surface of the medical device or subject's body. The method comprises the steps of: providing at least one surface of (i) a medical device or (ii) a subject's body, wherein the at least one surface comprises microorganisms and/or biofilm-embedded microorganisms attached thereto; and contacting the least one surface with a composition, whereby at least a portion of the microorganisms and/or biofilm embedded microorganisms are removed from the at least one surface or the number of microorganisms and/or biofilm embedded microorganisms attached to the at least one surface is reduced. The contact between the at least one surface and the composition should last for a period of time sufficient to remove at least a portion of the microorganisms and/or biofilm-embedded microorganisms from at least one surface of the medical device or subject's body or reduce the number of microorganisms and/or biofilm embedded microorganisms attached to the at least one surface.

In one embodiment, the medical device is submerged in the composition for at least 5 minutes. In another embodiment, the medical device is flushed with the composition. When medical device is a piece of tubing, such as dental drain tubing, the composition may be poured into the dental drain tubing and both ends of the tubing may be clamped, such that the composition is retained within the lumen of the tubing. The tubing is then allowed to remained filled with the composition for a period of time sufficient to remove or combat at least a portion of the microorganisms and/or biofilm embedded microorganisms from at least one surface of the medical device, generally for at least about 1 minutes to about 48 hours. In yet another embodiment, the dental tubing may be flushed by pouring the composition into the lumen of the dental tubing for an amount of time sufficient to prevent, reduce or remove microorganism and/or biofilm embedded microorganisms.

In one embodiment, the medical device is dipped in the composition for a period of time ranging from about 5 seconds to about 120 minutes at a temperature ranging from about 25° C. to about 80° C. In another embodiment, the medical device is dipped in the composition for about 60 minutes at a temperature of about 45° C. The medical device is then removed from the composition, and the composition is allowed to dry. The medical device may be placed in an oven or other heated environment for a period of time sufficient for the composition to dry. Preferably, the medical device is placed in a heated environment having a temperature of about 25° C. to about 85° C., for about 3 minutes to about 30 minutes. Preferably, the medical device is placed in an oven at a temperature ranging from about 50° C. to about 70° C. for about 10 minutes to 15 about 20 minutes.

Pharmaceutical Compositions and Formulations

The invention also encompasses the use of pharmaceutical compositions comprising α-lipoic acid or an analog thereof, for inhibiting or disrupting microorganism growth or the formation of biofilms on a surface of a subject's body. Such a pharmaceutical composition may consist of the compound α-lipoic acid or an analog thereof in a form suitable for administration to a subject. The compound α-lipoic acid or an analog thereof may be present in the pharmaceutical composition in the form of a physiologically acceptable salt, such as in combination with a physiologically acceptable cation, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Administration/Dosing

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

In one embodiment, the present invention is directed to a packaged pharmaceutical composition comprising a container holding a therapeutically effective amount of a compound of the invention, alone or in combination with a second pharmaceutical agent; and instructions for using the compound to prevent or reduce the growth or proliferation of microorganisms or biofilm-embedded microorganisms on at least one surface of a medical device or a subject's body.

Routes of Administration

Routes of administration of any of the compositions of the invention include rectal, transdermal, transmucosal (e.g., sublingual, lingual, (trans)buccal, (trans)urethral, vaginal (e.g., trans- and perivaginally), (trans)rectal, intravesical, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically-or naturally derived.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Unless otherwise noted, all starting materials were obtained from commercial suppliers and used without purification.

Example 1: Anticolonization Activity of Central Venous Catheters Impregnated with α-Lipoic Acid, Gentamicin, or the Combination of α-Lipoic Acid and Gentamicin Against Common Pathogens In this example, segments of 7 French triple lumen polyurethane central venous catheters were impregnated with α-lipoic acid using the method described elsewhere (U.S. Pat. No. 6,589,591) and were subjected to zones of inhibition. Briefly, α-lipoic acid was dissolved in 88% formic acid (at a final solution concentration of 50 mg/ml). 85% ortho-Phosphoric acid and glycerol were then added to the solution at 79:8:13 (v/v/v) (formic acid:ortho-phosphoric acid:glycerol). After mixing the solution, 300 mg/ml of potassium chloride was added to the final solution and mixed.

Catheter segments were then placed in the impregnating solution at 55° C. with agitation for 1 hour in the dark. Catheter segments were then removed from the solution and dried under a fume hood overnight in the dark. Catheter segments were rinsed with deionized water the next day and let dry for another 18 hours in the dark. After the impregnation process and drying, one-centimeter segments of impregnated catheters were individually placed in 1 ml of $10^5$ cfu/ml suspensions of methicillin-sensitive *Staphylococcus epidermidis* (MSSE), methicillin-resistant *Staphylococcus epidermidis* (MRSE), methicillin-resistant *Staphylococcus aureus* (MRSA), *Klebsiella pneumoniae*, *Escherichia coli*, or *Proteus mirabilis* in trypticase soy broth (TSB) at 37° C. for 24 hours. One-centimeter segments of non-impregnated catheters were also incubated individually in each bacterial suspension at 37° C. for 24 hours as controls. Catheter segments were removed from each bacterial suspension after this period, shaken to remove excess broth containing free-floating bacteria from their surfaces, placed in 1 ml of normal saline, sonicated for 5 minutes, and vortexed for 30 seconds.

Aliquots of each suspension and subsequent dilutions were cultured quantitatively. Table 1 displays the culture results for this experiment, which indicate that catheter segments treated with α-lipoic acid had substantially fewer or no bacterial cells adhered to them and were less likely to become colonized compared to the control uncoated catheter segments.

TABLE 1

Bacterial colony counts extracted from central venous catheters after incubation in bacterial suspension.

| Organism | Control | Lipoic acid (50 mg/ml) |
|---|---|---|
| MSSE | $4.6 \times 10^6$ | 10 |
| MRSE | $7.4 \times 10^5$ | 60 |
| MRSA | $8.3 \times 10^6$ | 0 |
| *Escherichia coli* | $5.0 \times 10^6$ | $1.4 \times 10^4$ |
| *Klebsiella pneumoniae* I | $5.6 \times 10^6$ | $1.1 \times 10^6$ |
| *Klebsielle pneuminiae* II | $5.6 \times 10^6$ | $9.0 \times 10^3$ |
| *Proteus mirabilis* | $6.3 \times 10^6$ | 0 |

Example 2: Antimicrobial Activity of Central Venous Catheters Impregnated with α-Lipoic Acid, Gentamicin, or the Combination of α-Lipoic Acid and Gentamicin Against Common Pathogens Based on Zone of Inhibition To evaluate the antimicrobial activity of central venous catheters treated with α-lipoic acid or its combination with gentamicin, segments of 7 French triple lumen polyurethane central venous catheters were impregnated with α-lipoic acid, gentamicin, or the combination of lipoic acid and gentamicin using the same patented method described in Example 1 with 50 mg/ml of each agent (for the final solution volume). After the impregnation process and drying, zones of inhibition were performed on one-centimeter segments according to a modified Kirby-Bauer method against MSSE, MRSE, MRSA, *K. pneumoniae*, *E. coli*, *P. mirabilis*, *Pseudomonas aeruginosa*, and *Candida albicans*. Each segment was half embedded in the center of a Muller-Hinton agar plate that had been previously inoculated with an individual organism. Prior to placing the catheter segments in agar, each organism was grown for 18 hours in TSB to a concentration of 0.5 McFarland ($10^8$ cfu/ml). A cotton swab was placed in the suspension and streaked across the surface of the Muller-Hinton agar plate to cover the entire plate. All plates were placed in a 37° C. incubator for 24 hours. Zones were measured in mm after the incubation period (Table 2).

TABLE 2

Zones of inhibition produced by a-lipoic acid-impregnated central venous catheters.

| Organism | Gentamicin | Lipoic acid | Lipoic acid + Gentamicin |
|---|---|---|---|
| MSSE | 21 | 32 | 40 |
| MRSE | 22 | 22 | 38 |
| MRSA | 15 | 13 | 32 |
| *Escherichia coli* | 12 | 12 | 28 |
| *Klebsiella pneumoniae* I | 13 | 20 | 27 |
| *Klebsielle pneuminiae* II | 0 | 18 | 25 |
| *Proteus mirabilis* | 14 | 12 | 24 |
| *Pseudomonas aeruginosa* | 5 | 5 | 26 |
| *Candida albicans* | 0 | 10 | 10 |

All zones are mm

Example 3: Antimicrobial Activity of Central Venous Catheters Impregnated with α-Lipoic Acid, Doxycycline, or the Combination of α-Lipoic Acid and Doxycycline Against Some Common Pathogens Based on Zone of Inhibition To evaluate the antimicrobial activity of central venous catheters treated with α-lipoic acid or its combination with doxycycline, segments of 7 French triple lumen polyurethane central venous catheters were impregnated with doxycycline or the combinations of α-lipoic acid and doxycycline using the same patented method described in Example 1 (U.S. Pat. No. 6,589,591) with 50 mg/ml of each agent (for the final solution volume). After the impregnation process and drying, zones of inhibition were performed on one-centimeter segments according to a modified Kirby-Bauer method against MSSE, MRSE, MRSA, *K. pneumoniae, E. coli, P. aeruginosa, P. mirabilis*, and *C. albicans* as described in Example 2. Zones of inhibition were measured in mm after the incubation period (Table 3).

TABLE 3

Zones of inhibition produced by a-lipoic acid-impregnated central venous catheters.

| Organism | Doxycycline | Lipoic acid | Lipoic acid + Doxycycline |
| --- | --- | --- | --- |
| MSSE | 21 | See Table 2 | 27 |
| MRSE | 35 | | 41 |
| MRSA | 22 | | 24 |
| Escherichia coli | 24 | | 27 |
| Klebsiella pneumoniae I | 17 | | 23 |
| Klebsielle pneuminiae II | 13 | | 16 |
| Proteus mirabilis | 4 | | 5 |
| Pseudomonas aeroginosa | 13 | | 18 |
| Candida albicans | 13 | | 17 |

All zones are mm

Example 4: Antimicrobial Activity of Central Venous Catheters Impregnated with Lipoamide, Levofloxacin, or the Combination of Lipoamide and Levofloxacin Against Common Pathogens Based on Zone of Inhibition To evaluate the antimicrobial activity of central venous catheters treated with lipoamide or its combination with levofloxacin, segments of 7 French triple lumen polyurethane central venous catheters were impregnated with levofloxacin or the combinations of lipoamide and levofloxacin using the same patented method described in Example 1 (U.S. Pat. No. 6,589,591) with 100 mg/ml (final solution volume) of each agent. After the impregnation process and drying, zones of inhibition were performed on one-centimeter segments according to a modified Kirby-Bauer method against MSSE, MRSE, MRSA, vancomycin-resistant *Enterococcus* (VRE), *K. pneumoniae, E. coli, P. aeruginosa, P. mirabilis*, and *C. albicans* as described in Example 2. Zones of inhibition were measured in mm after the incubation period (Table 4).

TABLE 4

Zones of inhibition produced by lipoamide-impregnated catheters.

| | Levofloxacin | Lipoamide | Lipoamide + Levofloxacin |
| --- | --- | --- | --- |
| MSSE | 30 | 24 | 48 |
| MRSE | 31 | 16 | 51 |

TABLE 4-continued

Zones of inhibition produced by lipoamide-impregnated catheters.

| | Levofloxacin | Lipoamide | Lipoamide + Levofloxacin |
| --- | --- | --- | --- |
| MRSA | 21 | 10 | 39 |
| VRE | 7 | 4 | 18 |
| Escherichia coli | 27 | 10 | 37 |
| Proteus mirabilis | 31 | 13 | 45 |
| Klebsiella pneumoniae I | 24 | 12 | 43 |
| Klebsiella pneumoniae II | 18 | 13 | 30 |
| Pseudomonas aeroginosa | 19 | 18 | 41 |
| Candida albicans | 0 | 6 | 6 |

Example 5: Antimicrobial Activity of Central Venous Catheters Impregnated with Lipoamide, Doxycycline, or the Combination of Lipoamide and Doxycycline Against Common Pathogens Based on Zone of Inhibition To evaluate the antimicrobial activity of central venous catheters treated with lipoamide or its combination with doxycycline, segments of 7 French triple lumen polyurethane central venous catheters were impregnated with doxycycline or the combinations of lipoamide and doxycycline using the same patented method described in Example 1 (U.S. Pat. No. 6,589,591) with 100 mg/ml (final solution volume) of each agent. After the impregnation process and drying, zones of inhibition were performed on one-centimeter segments according to a modified Kirby-Bauer method against MSSE, MRSE, MRSA, vancomycin-resistant *Enterococcus* (VRE), *K. pneumoniae, E. coli, P. aeruginosa, P. mirabilis*, and *C. albicans* as described in Example 2. Zones of inhibition were measured in mm after the incubation period (Table 5).

TABLE 5

Zones of inhibition produced by lipoamide-impregnated catheters.

| | Doxycycline | Lipoamide | Lipoamide + Doxycycline |
| --- | --- | --- | --- |
| MSSE | 20 | See Table 4 | 32 |
| MRSE | 38 | | 46 |
| MRSA | 19 | | 30 |
| VRE | 30 | | 41 |
| Escherichia coli | 22 | | 34 |
| Proteus mirabilis | 0 | | 11 |
| Klebsiella pneumoniae I | 19 | | 28 |
| Klebsiella pneumoniae II | 7 | | 21 |
| Pseudomonas aeroginosa | 11 | | 28 |
| Candida albicans | 5 | | 18 |

Example 6: Antimicrobial Activity of Central Venous Catheters Impregnated with Dihydrolipoic Acid, Against Common Pathogens Based on Zone of Inhibition To evaluate the antimicrobial activity of central venous catheters treated with dihydrolipoic acid, segments of 7 French triple lumen polyurethane central venous catheters were impregnated with dihydrolipoic acid using the same patented method described in Example 1 (U.S. Pat. No. 6,589,591) with 25 mg/ml (final solution volume) of the agent. After the impregnation process and drying, zones of inhibition were performed on one-centimeter segments according to a modified Kirby-Bauer method against MSSE, MRSE, MRSA, vancomycin-resistant *Enterococcus* (VRE), *K. pneumoniae, E. coli, P. aeruginosa, P. mirabilis*, and *C. albicans* as described in Example 2. Zones of inhibition were measured in mm after the incubation period (Table 6).

TABLE 6

Zones of inhibition produced by dihydrolipoic acid-impregnated catheters.

|  | Dihydrolipoic acid |
| --- | --- |
| MSSE | 25 |
| MRSE | 21 |
| MRSA | 24 |
| VRE | 14 |
| Escherichia coli | 0 |
| Proteus mirabilis | 0 |
| Klebsiella pneumoniae I | 0 |
| Klebsiella pneumoniae II | 0 |
| Pseudomonas aeroginosa | 11 |
| Candida albicans | 13 |

Example 7: Anticolonization Activity of Central Venous Catheters Impregnated with Lipoamide Against Common Pathogens To evaluate the anticolonization/antimicrobial activity of central venous catheters treated with lipoamide, segments of 7 French triple lumen polyurethane central venous catheters were impregnated with lipoamide using the same patented method described in Example 1 (U.S. Pat. No. 6,589,591) with 100 mg/ml (final solution volume) of the agent. After the impregnation process and drying, Catheter segments were then placed in the impregnating solution at 55° C. with agitation for 1 hour in the dark. Catheter segments were then removed from the solution and dried under a fume hood overnight in the dark. Catheter segments were rinsed with deionized water the next day and let dry for another 18 hours in the dark. After the impregnation process and drying, one-centimeter segments of impregnated catheters were individually placed in 1 ml of $10^5$ cfu/ml suspensions of MRSE, MRSA, or *P. aeruginosa* in trypticase soy broth (TSB) at 37° C. for 24 hours. One-centimeter segments of non-impregnated catheters were also incubated individually in each bacterial suspension at 37° C. for 24 hours as controls. Catheter segments were removed from each bacterial suspension after this period, shaken to remove excess broth containing free-floating bacteria from their surfaces, placed in 1 ml of normal saline, sonicated for 5 minutes, and vortexed for 30 seconds.

Aliquots of each suspension and subsequent dilutions were cultured quantitatively. Table 7 illustrates the culture results for this experiment, which indicate that catheter segments treated with lipoamide had substantially fewer or no bacterial cells adhered to them and were less likely to become colonized compared to the control uncoated catheter segments.

TABLE 7

Mean bacterial colony counts extracted from each type of catheter after exposure of bacteria.

| Organism | Control untreated | Lipoamide-treated |
| --- | --- | --- |
| MRSE | 7555000 | 0 |
| MRSA | 4226667 | 0 |
| Pseudomonas aeruginosa | 1896667 | 210000 |

Example 8: Anticolonization Activity of Central Venous Catheters Impregnated with Dihydrolipoic Acid Against Common Pathogens To evaluate the anticolonization/antimicrobial activity of central venous catheters treated with dihydrolipoic acid, segments of 7 French triple lumen polyurethane central venous catheters were impregnated with dihydrolipoic acid using the same patented method described in Example 1 (U.S. Pat. No. 6,589,591) with 25 mg/ml (final solution volume) of the agent. After the impregnation process and drying, Catheter segments were then placed in the impregnating solution at 55° C. with agitation for 1 hour in the dark. Catheter segments were then removed from the solution and dried under a fume hood overnight in the dark. Catheter segments were rinsed with deionized water the next day and let dry for another 18 hours in the dark. After the impregnation process and drying, one-centimeter segments of impregnated catheters were individually placed in 1 ml of $10^5$ cfu/ml suspensions of MRSE, MRSA, or *K. pneumoniae* in trypticase soy broth (TSB) at 37° C. for 24 hours. One-centimeter segments of non-impregnated catheters were also incubated individually in each bacterial suspension at 37° C. for 24 hours as controls. Catheter segments were removed from each bacterial suspension after this period, shaken to remove excess broth containing free-floating bacteria from their surfaces, placed in 1 ml of normal saline, sonicated for 5 minutes, and vortexed for 30 seconds.

Aliquots of each suspension and subsequent dilutions were cultured quantitatively. Table 8 illustrates the culture results for this experiment, which indicate that catheter segments treated with dihydrolipoic acid had substantially fewer bacterial cells adhered to them and were less likely to become colonized compared to the control uncoated catheter segments.

TABLE 8

Mean bacterial colony counts extracted from each type of catheter after exposure to bacteria.

| Organism | Control | Dihydrolipoic acid |
| --- | --- | --- |
| MRSE | 6155000 | 380 |
| MRSA | 4000000 | 50 |
| Klebsiella pneumoniae | 1896667 | 280000 |

As illustrated in Tables 1-8, α-lipoic acid and analogs thereof (such as lipoamide, and dihydrolipoic acid) exhibited unexpected intrinsic antimicrobial activities. More importantly, α-lipoic acid or lipoamide in combination with an antibiotic (such as but not limited to gentamicin, doxycycline or levofloxacin) displays unexpected synergistic antimicrobial activity.

In summary, the current invention has a broad antimicrobial and antibiofilm utility, particularly in medical device-related infections. α-Lipoic acid or its analogs may be applied to indwelling or implantable medical devices alone or in combination with antibiotic or antiseptic agents to prevent, reduce or treat infections associated with medical devices. As demonstrated herein, α-lipoic acid possesses a broad-spectrum of intrinsic antimicrobial activity, the non-antibiotic characteristic of this compound can potentially make it an unlikely candidate for the development of resistance and a suitable choice to be combined with antibiotics or antiseptics for coating, impregnating, or treating medical devices against pathogenic infections.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for preventing or reducing the growth or proliferation of microorganisms and biofilm-embedded microorganisms on at least one surface of a medical device or subject's body, comprising the steps of:
providing at least one surface of (i) a medical device, or (ii) a subject's body;
providing a composition comprising α-lipoic acid or an analog thereof selected from the group consisting of lipoamide, dihydrolipoic acid, dihydrolipoamide, an ester derivative of α-lipoic acid, an ester derivative of dihydrolipoic acid, asparagusic acid, an ester derivative of asparagusic acid, 3,3'-dimercapto-isobutyric acid, an ester derivative of 3,3'-dimercapto-isobutyric acid, any salt or solvate thereof, or any combinations thereof, wherein the ester derivative is a methyl, ethyl, propyl, isopropyl, n-butyl, sec-butyl, isobutyl, tert-butyl, n-pentyl, n-hexyl, benzyl, or stearyl ester, and at least one antimicrobial agent selected from the group consisting of doxycycline, levofloxacin, and gentamicin; and
contacting the at least one surface with the composition in an amount sufficient to prevent or reduce the growth or proliferation of microorganisms and biofilm-embedded microorganisms on the at least one surface.

2. The method of claim 1, wherein in (ii) the subject is a mammal.

3. The method of claim 2, wherein the mammal is human.

4. The method of claim 1, wherein α-lipoic acid or an analog thereof and the at least one antimicrobial agent act synergistically to prevent or reduce the growth or proliferation of microorganisms and biofilm-embedded microorganisms on the at least one surface.

5. The method of claim 1, wherein the composition is contacted with the at least one surface for a period of time sufficient to form a coating of the composition on the at least one surface.

6. The method of claim 1, wherein the composition is contacted with the at least one surface of the medical device in (i) by flushing the at least one surface of the medical device with the composition for a period of time sufficient to prevent or reduce the growth or proliferation of microorganisms and biofilm-embedded microorganisms on the at least one surface of the medical device.

7. The method of claim 1, wherein the at least one surface of the medical device in (i) is non-metallic and the composition further comprises an acidic solution and glycerol.

8. The method of claim 7, wherein the acidic solution comprises a short chain monocarboxylic acid and ortho-phosphoric acid.

9. The method of claim 8, wherein the acidic solution comprises monocarboxylic acid, ortho-phosphoric acid and glycerol in a ratio of 79:8:13 (v/v/v).

10. The method of claim 1, wherein the at least one surface of the medical device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof.

11. The method of claim 10, wherein the composition is applied to at least one surface to form a first layer.

12. The method of claim 11, wherein a second composition comprising a cyanoacrylate is applied on the first layer to form a second layer.

13. The method of claim 10, wherein the matrix component comprises hide powder and collagen, wherein the hide powder is at an 5% to 50% (w/v) concentration and the collagen is at an 0.1% to 20% (w/v) concentration.

14. The method of claim 10, wherein the acidic component is an acid solvent or acidic solution.

15. The method of claim 10, wherein the glycerol is present in the matrix component at a concentration between 0.5% and 10%.

16. The method of claim 10, wherein a cyanoacrylate coat is applied to the at least one surface as a primer before applying the composition.

17. A coated medical device having at least one surface, wherein the at least one surface is coated with a composition, wherein the coating of the at least one surface prevents or reduces the growth or proliferation of microorganisms and biofilm-embedded microorganisms on the at least one surface, wherein the composition comprises α-lipoic acid or an analog thereof selected from the group consisting of lipoamide, dihydrolipoic acid, dihydrolipoamide, an ester derivative of α-lipoic acid, an ester derivative of dihydrolipoic acid, asparagusic acid, an ester derivative of asparagusic acid, 3,3'-dimercapto-isobutyric acid, an ester derivative of 3,3'-dimercapto-isobutyric acid, any salt or solvate thereof, or any combinations thereof, wherein the ester derivative is a methyl, ethyl, propyl, isopropyl, n-butyl, sec-butyl, isobutyl, tert-butyl, n-pentyl, n-hexyl, benzyl, or stearyl ester, and at least one antimicrobial agent selected from the group consisting of doxycycline, levofloxacin, and gentamicin.

18. The device of claim 17, wherein the at least one surface of the medical device is non-metallic and the composition further comprises an acidic solution and glycerol.

19. The device of claim 18, wherein the acidic solution comprises a short chain monocarboxylic acid and ortho-phosphoric acid.

20. The device of claim 19, wherein the acidic solution comprises monocarboxylic acid, ortho-phosphoric acid and glycerol in a ratio of 79:8:13 (v/v/v).

21. The method of claim 1 further comprising: removing any amount of composition in excess of the amount sufficient to prevent or reduce the growth or proliferation of microorganisms and biofilm-embedded microorganisms on the at least one surface; and drying the at least one surface.

22. The device of claim 17, wherein the at least one surface of the medical device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof.

23. The device of claim 22, wherein the at least one surface is coated with a second composition comprising a cyanoacrylate.

24. The device of claim 22, wherein the matrix component comprises hide powder and collagen, wherein the hide powder is at an 5% to 50% (w/v) concentration and the collagen is at an 0.1% to 20% (w/v) concentration.

25. The device of claim 22, wherein the acidic component is an acid solvent or acidic solution.

26. The device of claim 22, wherein the glycerol is present in the matrix component at a concentration between 0.5% and 10%.

27. A method for removing at least a portion of or reducing the number of microorganisms and biofilm-embedded microorganisms attached to at least one surface of a medical device or subject's body, the method comprising the steps of:
providing at least one surface of (i) a medical device or (ii) a subject's body, wherein the microorganisms and biofilm-embedded microorganisms are attached to the at least one surface,
providing a composition comprising α-lipoic acid or an analog thereof selected from the group consisting of lipoamide, dihydrolipoic acid, dihydrolipoamide, an ester derivative of α-lipoic acid, an ester derivative of dihydrolipoic acid, asparagusic acid, an ester derivative of asparagusic acid, 3,3'-dimercapto-isobutyric acid, an ester derivative of 3,3'-dimercapto-isobutyric acid, any salt or solvate thereof, or any combinations thereof, wherein the ester derivative is a methyl, ethyl, propyl, isopropyl, n-butyl, sec-butyl, isobutyl, tert-butyl, n-pentyl, n-hexyl, benzyl, or stearyl ester, and at least one antimicrobial agent selected from the group consisting of doxycycline, levofloxacin, and gentamicin; and,
contacting the composition with the at least one surface in an amount sufficient to remove at least a portion of or reduce the number of microorganisms and biofilm-embedded microorganisms attached to the at least one surface.

28. The method of claim 27, wherein in (ii) the subject is a mammal.

29. The method of claim 28, wherein the mammal is human.

30. The method of claim 21, wherein α-lipoic acid or an analog thereof and the at least one antimicrobial agent act synergistically to reduce or prevent the growth or proliferation of microorganisms and biofilm-embedded microorganisms on the at least one surface.

31. The method of claim 27, wherein the composition is contacted with the at least one surface for a period of time sufficient to form a coating of the composition on the at least one surface.

32. The method of claim 27, wherein the composition is contacted with the at least one surface of the medical device by flushing the at least one surface of the medical device with the composition for a period of time sufficient to remove at least a portion of or reduce the number of microorganisms and biofilm-embedded microorganisms attached to the at least one surface of the medical device.

33. The method of claim 27, wherein the at least one surface of the medical device in (i) is non-metallic and the composition further comprises an acidic solution and glycerol.

34. The method of claim 33, wherein the acidic solution comprises a short chain monocarboxylic acid and ortho-phosphoric acid.

35. The method of claim 34, wherein the acidic solution comprises monocarboxylic acid, ortho-phosphoric acid and glycerol in a ratio of 79:8:13 (v/v/v).

36. The method of claim 27, wherein the at least one surface of the medical device in (i) is metallic and the composition further comprises an acidic component, glycerol, and a matrix component selected from the group consisting of hide powder, collagen, gelatin, cartilage, tendon, ligament, bone, keratin, fibrin, albumin, globulin, hydroxylapatite, and any combinations thereof.

37. The method of claim 36, wherein the composition is applied to at least one surface to form a first layer.

38. The method of claim 37, wherein a second composition comprising a cyanoacrylate is applied on the first layer to form a second layer.

39. The method of claim 36, wherein the matrix component comprises hide powder and collagen, wherein the hide powder is at an 5% to 50% (w/v) concentration and the collagen is at an 0.1% to 20% (w/v) concentration.

40. The method of claim 36, wherein the acidic component is an acid solvent or acidic solution.

41. The method of claim 36, wherein the glycerol is present in the matrix component at a concentration between 0.5% and 10%.

42. The method of claim 36, wherein a cyanoacrylate coat is applied to the at least one surface as a primer before applying the composition.

43. A composition comprising α-lipoic acid or an analog thereof selected from the group consisting of lipoamide, dihydrolipoic acid, dihydrolipoamide, an ester derivative of α-lipoic acid, an ester derivative of dihydrolipoic acid, asparagusic acid, an ester derivative of asparagusic acid, 3,3'-dimercapto-isobutyric acid, an ester derivative of 3,3'-dimercapto-isobutyric acid, any salt or solvate thereof, or any combinations thereof, wherein the ester derivative is a methyl, ethyl, propyl, isopropyl, n-butyl, sec-butyl, isobutyl, tert-butyl, n-pentyl, n-hexyl, benzyl, or stearyl ester, and at least one antimicrobial agent selected from the group consisting of doxycycline, levofloxacin, and gentamicin, wherein the α-lipoic acid or an analog thereof and the at least one antimicrobial agent have synergistic antimicrobial activity.

44. The composition of claim 43, wherein the antimicrobial activity is selected from the group consisting of antibacterial, antimycobacterial, antifungal, antiviral and any combinations thereof.

45. The method of claim 11, wherein the first layer is allowed to dry.

46. The method of claim 12, wherein the second layer is allowed to dry.

47. The method of claim 37, wherein the first layer is allowed to dry.

48. The method of claim 38, wherein the second layer is allowed to dry.

* * * * *